United States Patent
Krushinski, Jr. et al.

[11] Patent Number: 6,133,290
[45] Date of Patent: Oct. 17, 2000

[54] 5-HT$_{1F}$ AGONISTS

[75] Inventors: Joseph Herman Krushinski, Jr., Indianapolis; John Mehnert Schaus, Zionsville, both of Ind.

[73] Assignee: Eli Lilly and Company, Indianapolis, Ind.

[21] Appl. No.: 09/334,157

[22] Filed: Jun. 16, 1999

Related U.S. Application Data

[60] Provisional application No. 60/094,940, Jul. 31, 1998.
[51] Int. Cl.$^7$ .................. A61K 31/454; C07D 401/04
[52] U.S. Cl. .................. 514/322; 514/322; 514/316; 514/306; 514/299; 514/234.5; 514/228.2; 514/253.09; 546/199; 546/187; 546/138; 546/112; 544/130; 544/58.4; 544/364
[58] Field of Search ........................ 546/187, 199, 546/138, 112; 514/322, 306, 316, 253.09, 234.5, 228.5, 299, 228.2

[56] References Cited

U.S. PATENT DOCUMENTS

| | | | |
|---|---|---|---|
| 5,532,240 | 7/1996 | Nakao et al. | 514/254 |
| 5,776,963 | 7/1998 | Strupczewski et al. | 514/373 |
| 5,792,763 | 8/1998 | Fritz et al. | 514/228.2 |

FOREIGN PATENT DOCUMENTS

| | | |
|---|---|---|
| 0135 781 | 3/1985 | European Pat. Off. . |
| 0 494 774 | 1/1992 | European Pat. Off. . |
| 0 733 628 | 3/1996 | European Pat. Off. . |
| 0 842 934 | 11/1997 | European Pat. Off. . |
| 0 875 513 | 4/1998 | European Pat. Off. . |
| WO 94/27998 | 12/1994 | WIPO . |
| WO 97/49698 | 12/1997 | WIPO . |

*Primary Examiner*—Mukund J. Shah
*Assistant Examiner*—Sudhaker B. Patel
*Attorney, Agent, or Firm*—Robert D. Titus

[57] ABSTRACT

The present invention relates to a compound of formula I:

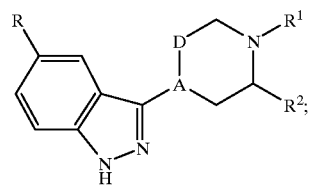

or a pharmaceutical acid addition salt thereof; which are useful for activating 5-HT$_{1F}$ receptors and inhibiting neuronal protein extravasation in a mammal.

11 Claims, No Drawings

5-HT$_{1F}$ AGONISTS

This application claims the benefit of priority from U.S. Provisional Application No. 60/094940 filed Jul. 31, 1998.

BACKGROUND OF THE INVENTION

Theories regarding the pathophysiology of migraine have been dominated since 1938 by the work of Graham and Wolff. *Arch. Neurol. Psychiatry,* 39:737–63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. Humphrey, et al., *Ann. NY Acad. Sci.,* 600:587–600, 1990. Recent work by Moskowitz has shown, however, that the occurrence of migraine headaches is independent of changes in vessel diameter. *Cephalalgia,* 12:5–7, 1992.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology,* 43(suppl. 3):S16–S20 1993.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA,* 90:408–412, 1993. This 5-HT$_{1F}$ receptor exhibits a pharmacological profile distinct from any serotonergic receptor yet described. The high affinity of sumatriptan at this subtype, $K_i$=23 nM, suggests a role of the 5-HT$_{1F}$ receptor in migraine.

This invention relates to novel 5-HT$_{1F}$ agonists which inhibit peptide extravasation due to stimulation of the trigeminal ganglia, and are therefore useful for the treatment of migraine and associated disorders.

SUMMARY OF THE INVENTION

The present invention relates to a compound of formula I:

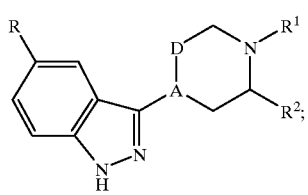

I or a pharmaceutical acid addition salt thereof; where:

A—D is CH—CH$_2$ or C=CH;

R is nitro, amino, halo, hydroxy, NR$^3$C(O)R$^4$, NR$^3$SO$_2$R$^5$, NHC(O)NR$^6$R$^7$, NHC(S)NR$^6$R$^7$, or NHCO$_2$R$^8$;

R$^1$ is hydrogen or C$_1$–C$_6$ alkyl;

R$^2$ is hydrogen or R$^1$ and R$^2$ combine, together with the 6 membered ring to which they are attached, to form a 6:5, 6:6, or 6:7 fused bicyclic ring;

R$^3$ is hydrogen or C$_1$–C$_6$ alkyl;

R$^4$ is C$_1$–C$_6$ alkyl or substituted C$_1$–C$_6$ alkyl;

R$^5$ is C$_1$–C$_6$ alkyl, phenyl, substituted phenyl, or (C$_1$–C$_6$ alkyl)$_2$amino;

R$^6$ and R$^7$ are independently C$_1$–C$_6$ alkyl, C$_3$–C$_6$ alkenyl, C$_3$–C$_8$ cycloalkyl, phenyl, substituted phenyl, phenyl (C$_1$–C$_4$ alkyl), or substituted phenyl(C$_1$–C$_4$ alkyl), or R$^6$ and R$^7$ combine, together with the nitrogen atom to which they are attached, form a pyrrolidine, piperidine, piperazine, 4-substituted piperazine, morpholine or thiomorpholine ring;

R$^8$ is C$_1$–C$_6$ alkyl, C$_3$–C$_6$ alkenyl, phenyl, substituted phenyl, or C$_3$–C$_8$ cycloalkyl.

This invention also relates to a pharmaceutical formulation comprising a compound of formula I, or a pharmaceutical acid addition salt thereof, and a pharmaceutical carrier, diluent, or excipient.

In addition, the present invention relates to a method for activating 5-HT$_{1F}$ receptors in mammals comprising administering to a mammal in need of such activation an effective amount of a compound of formula I, or a pharmaceutical acid addition salt thereof.

Moreover, the current invention relates to a method for inhibiting neuronal protein extravasation comprising administering to a mammal in need of such inhibition an effective amount of a compound of formula I, or a pharmaceutical acid addition salt thereof.

DETAILED DESCRIPTION OF THE INVENTION

One embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of formula I.

The use of a compound of formula I for the activation of the 5-HT$_{1F}$ receptor, for the inhibition of peptide extravasation in general or due to stimulation of the trigeminal ganglia specifically, and for the treatment of any of the disorders described above, are all embodiments of the present invention.

The general chemical terms used throughout have their usual meanings. For example, the term "6:5, 6:6, or 6:7 fused bicyclic ring" refers to moieties of the formula:

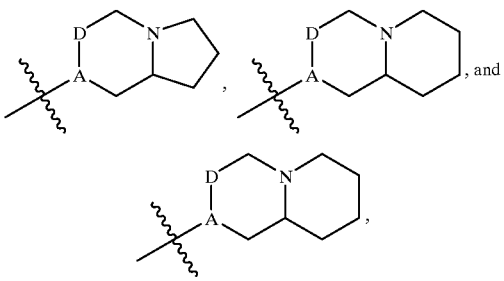

respectively.

The compounds of formula I where R¹ and R² combine, together with the 6 membered ring to which they are attached, to form a 6:5, 6:6, or 6:7 fused bicyclic ring (indolizinyl, quinolizinyl, or 1-azabicyclo[5.4.0]undecanyl ring respectively) contain a chiral center located in that bicyclic ring. This chiral center is located at the bridgehead carbon in the ring system. Furthermore, when R¹ and R² combine and A—D is CH—CH$_2$, the CH group of A—D is a chiral center as well. Such centers are designated "R" or "S". For the purposes of the present application, the numbering system for naming the substituents around the indazole ring and the R,R and S,S enantiomers are illustrated below where n is 0, 1, or 2 and A, D, E, R, R¹, R², and R³ are as defined above.

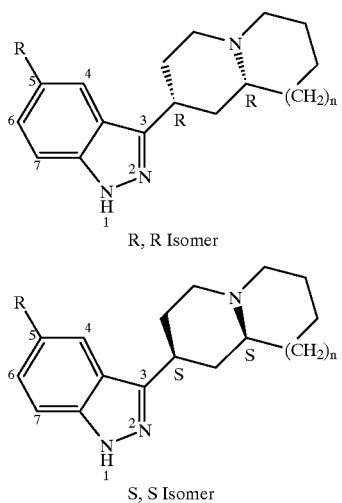

All enantiomers (S,R; R,S; S,S; R,R), diastereomers, and mixtures thereof, are included within the scope of the present invention.

The term "$C_1$–$C_4$ alkyl" refers to methyl, ethyl, n-propyl, isopropyl, cyclopropyl, n-butyl, isobutyl, sec-butyl, tert-butyl and cyclobutyl. The term "$C_1$–$C_6$ alkyl" includes those groups listed for $C_1$–$C_4$ alkyl and also refers to saturated, straight, branched, or cyclic hydrocarbon chains of 5 to 6 carbon atoms. Such groups include, but are not limited to, pentyl, pent-2-yl, pent-3-yl, neopentyl, hexyl, and the like. The term "$C_3$–$C_8$ cycloalkyl" refers to cyclopropyl, cyclobutyl, cyclopentyl, cyclohexyl, cycloheptyl, and cyclooctyl.

The term "$C_2$–$C_6$ alkenyl" refers to mono-unsaturated straight or branched hydrocarbon chains containing from 2 to 6 carbon atoms and includes, but is not limited to, vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like. The term "$C_3$–$C_6$ alkenyl" refers to the subset of $C_2$–$C_6$ alkenyl groups that contain from 3 to 6 carbon atoms.

The term "$C_2$–$C_6$ alkynyl" refers to straight or branched hydrocarbon chains containing 1 triple bond and from 2 to 6 carbon atoms and includes, but is not limited to, acetylenyl, propynyl, 2-butyn-4-yl, 1-butyn-4-yl, 1-pentyn-5-yl, 2-pentyn-5-yl and the like.

The terms "$C_1$–$C_6$ alkoxy" and "$C_1$–$C_4$ alkoxy" refer respectively to a $C_1$–$C_6$ alkyl and $C_1$–$C_4$ alkyl group bonded through an oxygen atom. The term "heteroaryloxy" refers to a heteroaryl or substituted heteroaryl group bonded through an oxygen atom. The term "aryloxy" refers to a phenyl or substituted phenyl group bonded through an oxygen atom. The term "$C_1$–$C_4$ acyl" refers to a formyl group or a $C_1$–$C_3$ alkyl group bonded through a carbonyl moiety. The term "$C_1$–$C_4$ alkoxycarbonyl" refers to a $C_1$–$C_4$ alkoxy group bonded through a carbonyl moiety.

The term "4-substituted piperazine" is taken to mean a piperazine ring substituted at the 4-position with a substituent selected from the group consisting of $C_1$–$C_6$ alkyl, ($C_1$–$C_4$ alkoxy)$C_1$–$C_6$ alkyl, phenyl, substituted phenyl, phenyl($C_1$–$C_4$ alkyl), substituted phenyl($C_1$–$C_4$ alkyl), heteroaryl, and heteroaryl($C_1$–$C_4$ alkyl).

The term "benzofused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

The term "halo" includes fluoro, chloro, bromo and iodo.

The term "heterocycle" is taken to mean an aromatic or non-aromatic 5- or 6-membered ring containing from 1 to 3 heteroatoms selected from: nitrogen, oxygen and sulfur, said ring optionally being benzofused. Non-aromatic rings include, for example, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl, and the like. Aromatic rings include furanyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused aromatic rings include isoquinolinyl, benzoxazolyl, benzthiazolyl, quinolinyl, benzofuranyl, benzothiophenyl, indolyl and the like.

The term "heteroaryl" is taken to mean an aromatic or benzofused aromatic heterocycle as defined in the previous paragraph.

The term "substituted $C_1$–$C_6$ alkyl" refers to a $C_1$–$C_6$ alkyl group that is substituted from 1 to 3 times independently with halo, hydroxy, phenyl, 2-phenylethylen-1-yl, diphenylmethyl, naphthyl, substituted phenyl, aryloxy, heterocycle, heteroaryloxy, $C_2$–$C_6$ alkenyl, $C_2$–$C_6$ alkynyl, $C_3$–$C_8$ cycloalkyl, $C_1$–$C_4$ alkoxy, $C_1$–$C_4$ alkoxycarbonyl, phenyl($C_1$–$C_4$ alkyl), substituted phenyl($C_1$–$C_4$ alkyl), or benzofused $C_4$–$C_8$ cycloalkyl.

The terms "substituted phenyl" and "substituted phenyl ($C_1$–$C_4$ alkyl)" are taken to mean that the phenyl moiety in either case is substituted with one substituent selected from the group consisting of halo, nitro, cyano, amino, trifluoromethyl, trifluoromethoxy, phenyl, benzoyl, $C_1$–$C_6$ alkyl, $C_1$–$C_6$ alkoxy, ($C_1$–$C_4$ alkyl)S(O)$_n$ where n is 0, 1, or 2, ($C_1$–$C_4$ alkyl)$_2$amino, $C_1$–$C_4$ acyl, or two to three substituents independently selected from the group consisting of halo, nitro, trifluoromethyl, $C_1$–$C_4$ alkyl, or $C_1$–$C_4$ alkoxy. The term "substituted naphthyl" refers to a naphthyl group that may be substituted in the same manner as a substituted phenyl group.

The terms "substituted heteroaryl" and "substituted heteroaryl($C_1$–$C_4$ alkyl)" are taken to mean that the heteroaryl moiety in either case is substituted with up to three substituents independently selected from: halo, cyano, nitro, hydroxy, $C_1$–$C_4$ alkoxy, $C_1$–$C_4$ alkyl, ($C_1$–$C_4$ alkyl)-S(O)$_n$, and phenyl-S(O)$_n$.

The term "amino protecting group" as used in this specification refers to a substituents commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as *"Greene"*.

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.,* 66:1, 1977.

The term "effective amount" means an amount of a compound of formula I which is capable of activating 5-HT$_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

The following group is illustrative of compounds contemplated within the scope of this invention:

The following group is illustrative of compounds contemplated within the scope of this invention:

5-(N-sec-butanesulfonyl)amino-3-(1-methylpiperidin-4-yl)-1H-indazole;

5-(N,N-dibutylaminosulfonyl)amino-3-(1-azabicyclo[5.4.0]undec-3-en-4-yl)-1H-indazole;

5-(N-isopropyl-N-sec-butanesulfonyl)amino-3-(1-ethylpiperidin-4-yl)-1H-indazole;

N-ethyl-N'-(3-(1,2,3,4,5,8-hexahydroindolizin-7-yl)-1H-indazol-5-yl)thiourea;

N-(3-propoxy)phenyl-N'-(3-(1-propylpiperidin-4-yl)-1H-indazol-5-yl)thiourea;

N-(3,4-difluoro)phenyl-N'-(3-(1,2,3,4,5,8-hexahydroindolizin-7-yl)-1H-indazol-5-yl)thiourea;

N-(3-fluoro-5-chloro)phenyl-N'-(3-(1-butylpiperidin-4-yl)-1H-indazol-5-yl)thiourea;

N-butyl-N'-(3-(octahydroindolizin-7-yl)-1H-indazol-5-yl)thiourea;

N-(2-butoxy)phenyl-N'-(3-(1-pentylpiperidin-4-yl)-1H-indazol-5-yl)thiourea hydrochloride;

N-(2-bromo-4-fluoro)phenyl-N'-(3-(1-hexylpiperidin-4-yl)-1H-indazol-5-yl)thiourea;

N-(4-trifluoromethyl)phenyl-N'-(3-(octahydro-2H-quinolizin-2-yl)-1H-indazol-5-yl)thiourea;

N-(2-hexen-6-yl)-N'-(3-(1-(2-pentyl)-1,2,3,4-tetrahydropyridin-4-yl)-1H-indazol-5-yl)urea;

N-(4-propylthio)phenyl-N'-(3-(1-methylpiperidin-4-yl)-1H-indazol-5-yl)urea;

N-(4-phenbutyl)-N'-(3-(1,4,5,6,7,8,9-heptahydroquinolizin-2-yl)-1H-indazol-5-yl)urea;

N-hexyl-N'-(3-(1-ethylpiperidin-4-yl)-1H-indazol-5-yl)urea;

N-(2-chloro)phenyl-N'-(3-(1-azabicyclo[5.4.0]undecan-4-yl)-1H-indazol-5-yl)urea;

N-(2-isopropoxy)phenyl-N'-(3-(1-propylpiperidin-4-yl)-1H-indazol-5-yl)urea;

N-(2-ethylthio)phenyl-N'-(3-(octahydroindolizin-7-yl)-1H-indazol-5-yl)urea;

N-(2-butyl)phenyl-N'-(3-(1-butylpiperidin-4-yl)-1H-indazol-5-yl)urea;

N-(3,4-difluoro)phenyl-N'-(3-(octahydro-2H-quinolizin-2-yl)-1H-indazol-5-yl)urea;

N-ethyl-N-phenyl-N'-(3-(1-cyclobutylpiperidin-4-yl)-1H-indazol-5-yl)urea;

5-(2-chlorophenoxy)carbonylamino-3-(1,4,5,6,7,8,9-heptahydroquinolizin-2-yl)-1H-indazole;

5-(3-propoxyphenoxy)carbonylamino-3-(1-cyclopentylpiperidin-4-yl)-1H-indazole;

5-(2-buten-4-yloxy)carbonylamino-3-(octahydro-2H-quinolizin-2-yl)-1H-indazole;

5-(2-iodophenoxy)carbonylamino-3-(1-pentyl-4-piperidin-4-yl)-1H-indazole;

5-cyclopropoxycarbonylamino-3-(1-azabicyclo[5.4.0]undecan-4-yl)-1H-indazole;

5-(acetyl)amino-3-(1-cyclohexylpiperidin-4-yl)-1H-indazole;

5-(4-phenoxybutanoyl)amino-3-(1,4,5,6,7,8,9-heptahydroquinolizin-2-yl)-1H-indazole;

5-benzoylamino-3-(1-hexylpiperidin-4-yl)-1H-indazole;

5-(4-fluorobenzoyl)amino-3-(1,4,5,6,7,8,9-heptahydroquinolizin-2-yl)-1H-indazole;

5-(4-fluorobenzoyl)amino-3-(1-methylpiperidin-4-yl)-1H-indazole;

5-(2-chlorobenzoyl)-N-ethylamino-3-(1,4,5,6,7,8,9-heptahydroquinolizin-2-yl)-1H-indazole;

5-(2-propylbenzoyl)amino-3-(1-ethylpiperidin-4-yl)-1H-indazole;

5-(3-heptyloxybenzoyl)amino-3-(1,4,5,6,7,8,9-heptahydroquinolizin-2-yl)-1H-indazole;

5-(2-cyanobenzoyl)amino-3-(1-propylpiperidin-4-yl)-1H-indazole;

5-(4-(propanoyl)benzoyl)amino-3-(1,4,5,6,7,8,9-heptahydroquinolizin-2-yl)-1H-indazole;
5-(2-bromo-3-iodo)benzoylamino-3-(1-cyclopropylpiperidin-4-yl)-1H-indazole;
5-(2-thienoyl)amino-3-(1,4,5,6,7,8,9-heptahydroquinolizin-2-yl)-1H-indazole;
5-(2-thienoyl)amino-3-(1-butylpiperidin-4-yl)-1H-indazole;
5-(3-thienoyl)amino-3-(1,4,5,6,7,8,9-heptahydroquinolizin-2-yl)-1H-indazole;
5-(2-furoyl)amino-3-(1-cyclobutylpiperidin-4-yl)-1H-indazole;
5-(3-furoyl)amino-3-(1,2,3,4,5,8-hexahydroindolizin-7-yl)-1H-indazole;
5-(3-furoyl)amino-3-(1-pentylpiperidin-4-yl)-1H-indazole;
5-(4-phenylbutanoyl)amino-3-(octahydro-2H-quinolizin-2-yl)-1H-indazole;
5-benzoylamino-3-(1-cyclopentylpiperidin-4-yl)-1H-indazole;
5-benzoylamino-3-(octahydroindolizin-7-yl)-1H-indazole;
5-(4-fluorobenzoyl)amino-3-(1-hexylpiperidin-4-yl)-1H-indazole;
5-(2-chlorobenzoyl)amino-3-(octahydroindolizin-7-yl)-1H-indazole;
5-(2-ethylbenzoyl)amino-3-(1-cyclohexylpiperidin-4-yl)-1H-indazole;
5-(2-hexyloxybenzoyl)amino-3-(octahydroindolizin-7-yl)-1H-indazole;
5-(4-(diethylamino)benzoyl)amino-3-(1-methylpiperidin-4-yl)-1H-indazole;
5-(2-(benzoyl)benzoyl)amino-3-(octahydroindolizin-7-yl)-1H-indazole;
5-(2-bromo-4-fluoro)benzoylamino-(3-(1-ethylpiperidin-4-yl)-1H-indazole;
5-(2-thienoyl)amino-3-(octahydroindolizin-7-yl)-1H-indazole;
5-(3-thienoyl)amino-3-(1-propylpiperidin-4-yl)-1H-indazole;
5-(3-thienoyl)amino-3-(octahydroindolizin-7-yl)-1H-indazole;
5-(2-furoyl)amino-3-(1-cyclopropylpiperidin-4-yl)-1H-indazole;
5-(3-furoyl)amino-3-(octahydro-2H-quinolizin-2-yl)-1H-indazole;

While all enantiomers, diastereomers, and mixtures thereof, are useful as 5-$HT_{1F}$ agonists, single enantiomers and single diastereomers are preferred. Furthermore, while all of the compounds of this invention are useful as 5-$HT_{1F}$ agonists, certain classes are preferred. The following paragraphs describe such preferred classes.

1) A—D is CH—$CH_2$;
2) A—D is C=CH;
3) R is halo, amino, or hydroxy;
4) R is $NR^3SO_2R^5$;
5) R is $NHC(O)NR^6R^7$;
6) R is $NHCO_2R^8$;
7) R is $NR^3C(O)R^4$;
8) $R^1$ is hydrogen or $C_1$–$C_4$ alkyl;
9) $R^1$ is methyl;
10) $R^2$ is hydrogen;
11) $R^1$ and $R^2$ combine, together with the 6 membered ring to which they are attached, to form a 6:5, 6:6, or 6:7 fused bicyclic ring;
12) $R^1$ and $R^2$ combine, together with the 6 membered ring to which they are attached, to form a 6:6 fused bicyclic ring;
13) when $R^1$ and $R^2$ combine, together with the 6 membered ring to which they are attached, to form a 6:5, 6:6, or 6:7 fused bicyclic ring, the compound is the R,R or S,R isomer;
14) when $R^1$ and $R^2$ combine, together with the 6 membered ring to which they are attached, to form a 6:5, 6:6, or 6:7 fused bicyclic ring, the compound is the S,S or R,S isomer;
15) $R^3$ is $C_1$–$C_4$ alkyl;
16) $R^3$ is methyl or hydrogen;
17) $R^4$ is selected from $C_3$–$C_6$ alkenyl; $C_3$–$C_6$ cycloalkyl; phenyl($C_1$–$C_4$ alkylene); $C_1$–$C_4$ alkyl ω-substituted with phenoxy; $C_1$–$C_4$ alkyl ω-substituted with $C_1$–$C_4$ alkoxy; phenyl monosubstituted with halo; phenyl monosubstituted with $C_1$–$C_4$ alkoxy; phenyl monosubstituted with $C_1$–$C_4$ alkyl; $C_1$–$C_4$ alkylthio, $C_1$–$C_4$ acyl; phenyl disubstituted with substitutents selected from halo, $C_1$–$C_4$ alkyl, $C_1$–$C_4$ alkoxy and nitro; heterocycle; furyl optionally substituted with $C_1$–$C_4$ alkyl, $C_1$–$C_4$ alkoxy, or halo; thienyl optionally substituted with halo, $C_1$–$C_4$ alkyl or $C_1$–$C_4$ alkoxy; pyridinyl optionally substituted with halo, $C_1$–$C_4$ alkyl or $C_1$–$C_4$ alkoxy;
18) $R^4$ is selected from: phenyl monosubstituted with chloro; phenyl monosubstituted with fluoro; phenyl monosubstituted with methoxy; phenyl monosubstituted with methyl; phenyl monosubstituted with trifluoromethyl; phenyl disubstituted with halo; pyrazinyl; and isoxazolyl;
19) $R^4$ is selected from: allyl; cyclopropyl; cyclobutyl; methoxymethyl; ethoxymethyl; phenyl; 2-phenylethylen-1-yl; 4-fluorophenyl; 2-chlorophenyl; cyano, nitro, benzoyl; 4-cyanophenyl; 4-nitrophenyl; 4-phenylphenyl; 4-methoxyphenyl; 2,4-dichlorophenyl; 2-furyl; 3-furyl; 2-thienyl; 3-thienyl; 3-methyl-2-thienyl; 5-methyl-2-thienyl; 3-pyridinyl; 4-pyridinyl; 6-halo-3-pyridinyl; 2-benzofuranyl;
20) $R^5$ is $C_1$–$C_4$ alkyl or di($C_1$–$C_4$ alkyl)amino;
21) $R^5$ is methyl, ethyl, phenyl, or dimethylamino;
22) $R^6$ is hydrogen;
23) $R^7$ is selected from: $C_1$–$C_4$ alkyl; $C_3$–$C_8$ alkenyl; phenyl monosubstituted with halo; phenyl($C_1$–$C_4$ alkylene);
24) $R^7$ is selected from: methyl; ethyl; propyl; isopropyl; phenyl; allyl; 4-fluorophenyl; 4-chlorophenyl; benzyl; phenethyl;
25) $R^6$ and $R^7$ taken together with the nitrogen to which they are attached form a morpholine ring;
26) $R^6$ and $R^7$ taken together with the nitrogen to which they are attached form a thiomorpholine ring;
27) $R^6$ and $R^7$ taken together with the nitrogen to which they are attached form a pyrrolidine ring;
28) $R^6$ and $R^7$ taken together with the nitrogen to which they are attached form a piperidine ring;
29) $R^6$ and $R^7$ taken together with the nitrogen to which they are attached form a pyrrolidine ring;
30) $R^6$ and $R^7$ taken together with the nitrogen to which they are attached form a piperazine ring;
31) $R^6$ and $R^7$ taken together with the nitrogen to which they are attached form a 4-substituted piperazine ring;
32) $R^8$ is $C_1$–$C_4$ alkyl, $C_3$–$C_6$ alkenyl, $C_3$–$C_8$ cycloalkyl; phenyl monosubstituted with $C_1$–$C_4$ alkoxy or halo;
33) $R^8$ is selected from: methyl, ethyl, propyl, allyl, cyclopentyl, 4-methoxyphenyl, and 4-fluorophenyl;

34) the compounds of the Examples section;
35) the compound is an acid addition salt;
36) the compound is the hydrochloride salt;
37) the compound is the oxalate salt; and
38) the compound is the fumarate salt.

It will be understood that the above classes may be combined to form additional preferred classes.

It is preferred that the mammal to be treated by the administration of compounds of this invention is human.

The compounds of formula I may be prepared from indoles of formula II as illustrated in Scheme 1 below where A, D, R, $R^1$, and $R^2$ are as defined above.

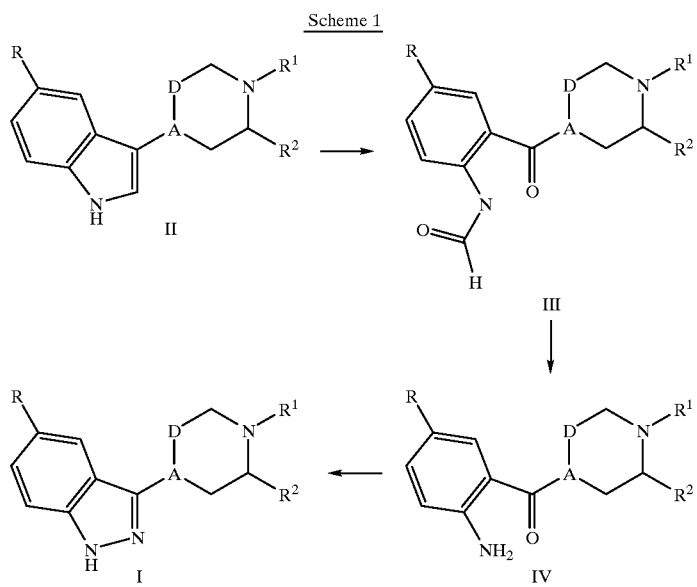

Scheme 1

Compounds of formula III may be prepared by adding a solution of about 2 to 2.5 equivalents of a periodate, typically sodium periodate in water, to a compound of formula II dissolved in a suitable solvent, typically a mixture of methanol and water. Generally, in order to facilitate dissolution in this methanol/water solvent system, a salt of a compound of formula II will be employed, e.g., the hydrochloride, or an acid will be added to the reaction mixture to form a salt while reacting, e.g., methanesulfonic acid. The reaction may be performed at temperatures ranging from 0° C. to the reflux temperature of the reaction mixture for from 8 hours to 2 weeks but is usually performed at ambient temperatures. In certain cases, e.g., when R is nitro, the deformylation may occur spontaneously during the periodate oxidation step. Thus, the chemistry described in the next paragraph may not be required for all compounds of formula II used in the above reaction.

In cases where a separate step is necessary to remove the formyl group, a compound of formula IV may prepared by treating a compound of formula III with an excess of an appropriate base dissolved in a lower alkanol, typically sodium hydroxide in methanol. This reaction may be performed at temperatures ranging from ambient to the reflux temperature of the mixture for from 1 to 24 hours. Typically, the reaction is performed at about 45° C. for about 2 hours.

The indazoles of formula I may now be prepared by treating a compound of formula IV, dissolved in a suitable acidic solvent, with a solution of about 1 equivalent of a nitrite, typically sodium nitrite in water, to create an intermediate diazonium salt. Once the diazonium salt is formed, typically in about 15 minutes to 1 hour, it may be converted to the indazole product by adding this mixture to a large excess of sulfur dioxide, typically as a saturated solution in water. The addition of nitrite may be performed at temperatures ranging from −50° C. to about ambient temperature but is typically performed at about 0° C. The inverse addition of the diazonium salt to the sulfur dioxide solution may also be performed cold as described above but is usually performed at about 3° C. Once the additions are complete, the reaction may be run cold for a short time, e.g., from about 15 minutes to 1 hour, but is then allowed to warm to ambient temperature and stir for an additional 12 to 24 hours.

Since the compounds of this invention are amines, they are basic in nature and accordingly react with any of a number of inorganic and organic acids to form pharmaceutical acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

The compounds of formula II may be prepared by methods well known to one of ordinary skill in the art. For example, the compounds of formula II where $R^1$ is $C_1-C_6$ alkyl and $R^2$ is hydrogen may be prepared from piperid-4-ones as described in U.S. Pat. No. 5,708,008, the teachings of which are herein incorporated by reference. Compounds of formula II where $R^1$ is not $C_1-C_6$ alkyl may be prepared substantially as described in '008. These syntheses are illustrated below in Scheme 2 where X is hydroxy, halo, nitro, or amino, n is 0, 1, or 2 and $R^1$ and $R^2$ are as defined above.

Scheme 2

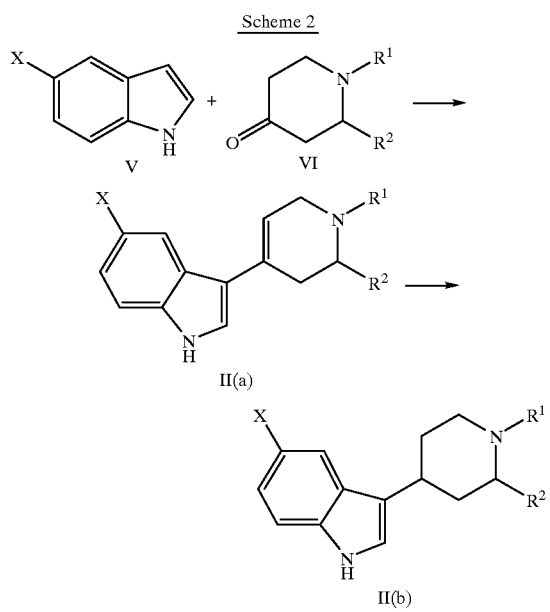

A 1H-indole of formula V may be condensed with a ketone of formula VI in the presence of a suitable base to give the corresponding compound of formula II(a). The reaction may be performed by adding the respective compounds of formula V and VI to a mixture of an appropriate base (typically sodium or potassium hydroxide) in a lower alkanol, typically methanol or ethanol. About 1 to about 5 equivalents of a compound of formula VI, relative to the compound of formula V are generally employed. A range of about 1.3 to 2.3 equivalents is preferred. The reaction is typically performed for about 0.25 to 24 hours.

If desired, compounds of formula II(a) may be hydrogenated over a precious metal catalyst to give the corresponding compounds of formula II(b). When X is bromo, a catalyst such as sulfided platinum on carbon, platinum oxide, or a mixed catalyst system of sulfided platinum on carbon with platinum oxide may be used to prevent hydrogenolysis of that bromo substituent during the reduction. (See Preparation 5 below). The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20 p.s.i. to 80 p.s.i., preferably from 50 p.s.i. to 60 p.s.i., at 0° C. to 60° C., preferably at ambient temperature to 40° C., for 1 hour to 3 days. Additional charges of hydrogen may be required to drive the reaction to completion depending on the specific substrate.

When the hydrogenation is performed with a compound of formula II(a) where X is hydroxy, nitro, or amino, more vigorous hydrogenation conditions may be used without disrupting the rest of the molecule. For example, a catalyst such as platinum or palladium on carbon may be utilized without substantially effecting deleterious side reactions.

In general, when X is nitro, that nitro group may be reduced to an amine at any convenient point in the syntheses outlined in Schemes 1 and 2 by well known methodology. See, e.g., Larock, "Comprehensive Organic Transformations", pgs. 412–415, VCH Publishers, New York, N.Y., 1989. Additionally, when X is nitro in compounds of formula II(a), that nitro group and the double bond may be hydrogenated simultaneously if desired to give a compound of formula II(b) where X is amino by many of the methods described by Larock for the nitro group alone. Furthermore, methods for selective reduction of a double bond in the presence of a nitro group are known in the art and one example of that transformation may be found in Preparation 10 below.

When X is amino, that amino group may be converted to bromo via the Sandmeyer reaction at any convenient point in the syntheses outlined in Schemes 1 and 2 by procedures taught by M. P. Doyle in *J. Org. Chem.*, 42:2426, 1977. If needed, it is preferred to perform the Sandmeyer reaction after the conversion of a compound of formula II(a) to a compound of formula II(b). These bromo compounds may be converted to their corresponding iodo compounds via metal-halogen exchange followed by the addition of elemental iodine.

The compounds of formula II(b) where X is nitro, amino, hydroxy or halo may be used as described in Scheme 1, or if desired, may first be further modified to provide the compounds of formula II where R is $NR^3C(O)R^4$, $NR^3SO_2R^5$, $NHC(O)NR^6R^7$, $NHC(S)NR^6R^7$, or $NHCO_2R^8$. As a preferred alternative, these modifications are performed after undergoing the chemistry described in Scheme 1 by directly analogous methods to that described below.

A compound of formula II(a) or II(b) where X is amino may be converted to a compound of formula II(a) or II(b) where X is $NR^3C(O)R^4$, $NR^3SO_2R^5$, $NHC(O)NR^6R^7$, $NHC(S)NR^6R^7$, or $NHCO_2R^8$ by procedures taught in the previously incorporated by reference U.S. Pat. No. 5,708,008.

The compounds of formula VI where $R^1$ and $R^2$ combine, together with the 6 membered ring to which they are attached, to form a 6:5, 6:6, or 6:7 fused bicyclic ring, may be prepared from methylvinyl ketone and an appropriate amino-dialkylacetal or -cyclic acetal according to the procedures found in *Tet. Let.*, 24:3281, 1983, and *J.C.S. Perk. I*, 447, 1986. These acetals are generally commercially available or can be synthesized by well known methods in the art from their corresponding commercially available 4-substituted butanals or 5-substituted pentanals. This chemistry is illustrated in Scheme 3, where m is 3,4, or 5, $R^9$ and $R^{10}$ are independently $C_1-C_4$ alkyl, or $R^9$ and $R^{10}$ taken together with the oxygen atoms, to which they are attached, form a 5 or 6 membered cyclic acetal, and n is 0, 1, or 2.

Scheme 3

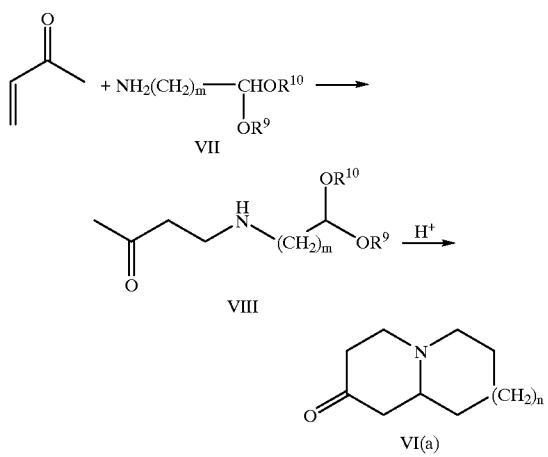

Compounds of formula VI(a) may be prepared by acid treatment of the addition product of methyl vinyl ketone and a compound of formula VII. A diethylacetal of formula VII is a preferred starting material for this reaction ($R^9$ and $R^{10}$ are ethyl). The reaction may be performed by first dissolving an appropriate aminoacetal of formula VII in an suitable solvent, typically diethyl ether at 0° C., and then adding approximately 1.7 equivalents of methyl vinyl ketone. Typically the reaction is allowed to stir at 0° C. for approximately 2 hours before acidification by addition of, or extraction with, aqueous hydrochloric acid. Typically, the organic layer is removed before heating the aqueous layer to approximately 100° C. for 1 hour. The resulting 7-octahydroindolizinone, 2-octahydro-2H-quinolizinone, or 4-(1-azabicyclo[5.4.0]undecan)ones of formula VI(a) may be isolated from the reaction mixture by adjusting the pH of the solution to alkaline and extracting with a water immiscible solvent such as ethyl acetate or dichloromethane.

Compounds of formula VI(a) prepared as described in Scheme 3 are racemic and, if used as described in Schemes 1–2, will produce racemic compounds of the invention. Compounds of the invention that are optically enhanced in one enantiomer may be obtained by resolving the compounds of formula VI(a) before use of these compounds as described in Scheme 2. Methods of resolving enantiomeric compounds of this type are well known in the art. For example, resolution can be achieved by use of chiral chromatography. Furthermore, racemic compounds of formula VI(a) may be converted to their corresponding diastereomeric mixture of salts by reaction with a chiral acid such as (+) or (-) tartaric acid. The diastereomers may then be separated and purified by recrystallization. Once separated, the salts may each be converted back to the chiral free base compounds of formula VI(a) by reacting the salts with an aqueous base, such as sodium hydroxide, then extracting the mixture with a common organic solvent. The optical purity in resolved compounds of formula VI(a) is maintained while undergoing the chemistry described in this application to afford optically pure compounds of the invention. As an alternative, when advantageous, the resolution techniques just discussed may be performed at any convenient point in the syntheses described in Schemes 1–2.

The indoles of formula V may be prepared by methods well known to one of ordinary skill in the art, such as that generally described in U.S. Pat. No. 4,443,451, the teachings of which are hereby incorporated by reference. While these indoles are generally commercially available, their preparations are also described in Robinson, *The Fischer Indole Synthesis*, Wiley, New York, 1983; Hamel, et al., *Journal of Organic Chemistry*, 59:6372, 1994; and Russell, et al., *Organic Preparations and Procedures International*, 17:391, 1985.

Compounds of formula V, VI, and VII are known in the art and, to the extent not commercially available, are readily synthesized by standard procedures commonly employed in the art such as those described herein.

The optimal time for performing the reactions of Schemes 1–3 can be determined by monitoring the progress of the reaction via conventional chromatographic techniques, e.g., thin layer chromatography and high performance liquid chromatography. Furthermore, it is usually preferred to conduct the reactions of Schemes 1–3 under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The intermediate compounds of this invention are preferably purified before their use in subsequent reactions. The intermediates and final products may be purified when, if in the course of their formation, they crystallize out of the reaction solution. In such a situation, the precipitate may be collected by filtration and washed with an appropriate solvent. Certain impurities may be removed from the organic reaction mixture by aqueous acidic or basic extraction followed by removal of the solvent by extraction, evaporation, or decantation. The intermediates and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. The terms and abbreviations used in the instant Preparations and Examples have their normal meanings unless otherwise designated. For example "° C.", "N", "mmol", "g", "mg", "mL", "M", and MS(FD) refer to degrees Celsius, normal or normality, millimole or millimoles, gram or grams, milligram or milligrams, milliliter or milliliters, molar or molarity, high performance liquid chromatography, and field desorption mass spectrometry respectively.

PREPARATIONS

Preparation 1

7-Octahydroindolizinone

Methylvinyl ketone (18.0 g, 256 mmol) was added dropwise to a solution of the 4,4-diethoxybutylamine (24.8 g, 154 mmol) in diethyl ether at 0° C. and stirred for one hour. The reaction was allowed to warm to room temperature and stir for 2 hours. The reaction was poured into 350 ml of 2N hydrochloric acid and the layers were separated. The aqueous layer was heated on a steam bath for 1 hour and then allowed to stir at 40° C. for 18 hours. The reaction was made basic with a sodium hydroxide solution and then extracted with methylene chloride. The extracts were dried over sodium sulfate and concentrated to give 20 g of an orange oil. This oil was distilled in vacuo at 74–84° C./5 mmHg to give 6.68 g of racemic product. (31%). MS(FD) (m/e): 139. $^1$H-NMR.

Preparation 2

Resolution of Racemic 7-Octahydroindolizinone

Step 1

Preparation of the (+)-Ditoluoyl Tartaric Acid Salts of 7-Octahydroindolizinone

The (+)-ditoluoyl tartaric acid monohydrate (19.7 g, 49 mmol) was dissolved in 100 ml of warm methanol and the racemic 7-octahydroindolizinone (6.86 g, 49 mmol) in 25 ml of methanol was added. The reaction was thoroughly mixed and allowed to stand at room temperature for about 18 hours. No precipitate had formed so the material was concentrated by boiling and ethyl acetate was added. At the point where solid began to form, the reaction was cooled to room temperature and a precipitate formed. This material was collected by filtration. The filter cake was recrystallized twice from methanol/acetonitrile to give 7.87 g a product which was approximately a 2:1 mixture of diastereomers. (31%). EA calculated for $C_8H_{13}NO.C_{20}H_{18}O_8$: Theory: C, 63.99; H, 5.95; N, 2.67. Found: C, 63.92; H, 5.98; N, 2.55. OR(DMSO, C=1.0) (α): 589 nm 72.6°; 365 nm 393.4°.

Step 2

Preparation of the Chiral 7-Octahydroindolizinone Free Amine

The (+)-ditoluoyl tartaric acid salt of 7-octahydroindolizinone (7.42 g, 14 mmol) from Step 1 was suspended in methylene chloride/0.5 M sodium hydroxide solution and stirred until no solid was visible. The layers were separated and the aqueous layer extracted with methylene chloride. The combined organic extracts were dried over sodium sulfate and concentrated to give 2.00 g of a light yellow oil. (100%). MS(FD) (m/e): 139.

Preparation 3

2-Octahydro-2H-Quinolizinone

Step 1

Preparation of 2-(3-Cyanopropyl)-1,3-Dioxolane

In a flame dried flask fitted with a nitrogen inlet, magnetic stirrer, and oil bath was dissolved the 2-(3-chloropropyl)-1,3-dioxolane (25.4 g, 169 mmol) in 70 ml of dimethylsulfoxide. Sodium cyanide (9.1 g, 186 mmol) in 100 ml of dimethylsulfoxide was added and the mixture was heated to 80° C. for 18 hours. The reaction was cooled to room temperature then poured onto ice water and stirred for 1 hour. The mixture was extracted thoroughly with diethyl ether, testing the aqueous after each extraction by TLC for the presence of product. The ether was washed with brine, dried over sodium sulfate, and concentrated in vacuo to give a colorless oil. The oil was purified by silica gel chromatography (50/50 ethyl acetate/hexane) to give 19.2 g of product. (80.7%). EA calculated for $C_7H_{11}NO_2$: Theory: C, 59.33; H, 7.63; N, 9.87. Found: C, 59.56; H, 7.85; N, 9.92. MS(FD+) (m/e): 142.

Step 2

Preparation of 2-(4-Aminobutyl)-1,3-Dioxolane

To a solution of 14.5 gm (10.3 mmol) 2-(3-Cyanopropyl)-1,3-dioxolane in anhydrous ammonia and ethanol was added 5% ruthenium on aluminum oxide. The reaction mixture was hydrogenated with an initial hydrogen pressure of 100 p.s.i. at ambient temperature for 32 hours. The reaction mixture was filtered and the filtrate concentrated under reduced pressure. The residue was purified by silica gel chromatography to give 12.0 gm (80.5%) of the product.

MS(FD+) (m/e): 146.

Step 3

Preparation of 2-Octahydro-2H-Quinolizinone

The 2-(4-aminobutyl)-1,3-dioxolane (2.45 g, 16.9 mmol) and methylvinyl ketone (2.4 ml, 28.7 mmol) were converted to product by the procedure of Preparation I to yield 100 mg. (3.85%). MS(FD+) (m/e): 153.

Preparation 4

5-Bromo-3-(1-Methyl-1,2,3,6-Tetrahydropyridin-4-yl)-1H-Indole

To a solution of 56.11 gm (306 mmol) potassium hydroxide in 300 mL methanol was added 38 mL (306 mMol) 1-methyl-4-piperidone followed by 30.0 gm (153 mMol) 5-bromo-1H-indole. The reaction mixture was stirred at the reflux temperature of the mixture for 18 hours. The reaction mixture was then cooled to ambient and diluted with 1.5 L water. The resultant white solid was filtered, washed sequentially with water and diethyl ether, and then dried under vacuum to give 44.6 gm of the title compound. (100%).

Preparation 5

5-Bromo-3-(1-Methylpiperidin-4-yl)-1H-Indole

To a solution of 5-bromo-3-(1-methyl-1,2,3,6-tetrahydro-4-pyridinyl)-1H-indole (44.6 g, 153 mmol) in 1.95 L tetrahydrofuran was added 9.0 gm platinum oxide. The reaction mixture was hydrogenated with an initial hydrogen pressure of 60 p.s.i. at ambient temperature for 24 hours. The reaction mixture was filtered and the filtrate concentrated under reduced pressure. The residue was recrystallized from acetonitrile to give 32.6 gm (73.7%) of the title compound as a white solid. MS(m/e): 293(M$^+$). EA calculated for $C_{14}H_{17}N_2Br$: C, 57.32; H, 5.96; N, 9.69. Found: C, 57.35; H, 5.84; N, 9.55.

Preparation 6

5-Bromo-3-(1-Methylpiperidin-4-yl)-1-Triisopropylsilylindole

To a 10° C. slurry of potassium hydride (1.6 g, 14.3 mmol, 35% in mineral oil) in tetrahydrofuran (40 mL) was added neat 5-bromo-3-(1-methyl-4-piperidinyl)indole (2.8 g, 9.5 mmol) portionwise over 30 minutes. The resulting reaction mixture was stirred at 0° C. for 1 hour. Triisopropylsilyl trifluoromethanesulfonate (3.1 mL, 11.4 mmol) was added dropwise over 20 minutes and a slight exotherm was observed. After stirring 2 hours at 0° C., the reaction was quenched with ice chips then diluted with water and methylene chloride. The layers were separated and the aqueous layer was extracted with methylene chloride. The organic extracts were combined, washed with brine, dried over sodium sulfate, and concentrated in vacuo to give 7.4 g of a clear colorless oil. Purification by chromatography (florisil, 50:50 methylene chloride:hexanes, then 100% methylene chloride, then 95:5 methylene chloride:methanol) provided 3.6 g (84.1%) of the title compound. MS(FD) 448, 450 (M$^+$).

Preparation 7

3-(1,2,3,4,5,8-Hexahydroindolizin-7-yl)-5-Nitro-1H-Indole

A mixture of 5-nitro-1H-indole (4.48 g, 27.6 mmol) and and 7-octahydroindolizinone (5.0 g, 35.9 mmol) in methanolic potassium hydroxide (10% potassium hydroxide in 50 mL of methanol) was heated to reflux for 3.5 hours. The reaction was diluted with water and the precipitate was collected by filtration. The filter cake was triturated with hot diethyl ether and filtered. The filter cake was recrystallized from methanol and dried to give 2.99 g of the title compound. (38.5%). Calculated for $C_{16}H_{17}N_3O_2$: Theory: C, 67.83; H, 6.05; N, 14.83. Found: C, 68.07; H, 6.27; N, 14.82.

MS(FD) (m/e): 283.

Preparation 8

3-(Octahydroindolizin-7-yl)-5-Amino-1H-Indole

The 3-(1,2,3,4,5,8-hexahydroindolizin-7-yl)-5-nitro-1H-indole (2.21 g, 6.90 mmol) was dissolved in 95 ml of ethanol and 50 ml of tetrahydrofuran. 5% palladium over carbon was added (550 mg) and the mixture was placed under an atmosphere of hydrogen, at an initial pressure of 60 psi, at room temperature, for 24 hours. The reaction mixture was filtered and the filtrate concentrated under reduced pressure to give 1.51 g of a purple foam. (85%).

Preparation 9

3-(1,2,3,4,5,8-Hexahydroindolizin-7-yl)-5-Chloro-1H-Indole

5-Chloro-1H-indole (1.00 g, 6.63 mmol) and 7-octahydroindolizinone (1.39 g, 9.95 mmol) were converted to product by the procedure of Preparation 4 to give 595 mg. (33.1%). EA calculated for $C_{16}H_{17}N_2Cl$: C, 70.45; H, 6.28; N, 10.27. Found: C, 70.60; H, 6.46; N, 10.28.

MS(FD) (m/e): 272.

Preparation 10

5-Nitro-3-(1-Methylpiperidin-4-yl)-1H-Indole

Triethylsilane (4.7 ml, 29.5 mmol) was added dropwise to a 0° C. solution of 5-nitro-3-(1-methyl-4-tetrahydropyridinly)indole (7.6 g, 29.5 mmol) in trifluoroacetic acid (50 ml). This resulting solution was stirred 2.5 hours at 0° C. then warmed to room temperature. The reaction mixture was concentrated in vacuo. The residue was dissolved in methylene chloride, cooled on an ice bath and 5N aqueous sodium hydroxide (110 ml) was added. The heterogeneous mixture was stirred 1 hour and the resulting precipitate was filtered and washed with water. Drying under vacuum yielded 5.0 g (65.3%) of the title compound. mp 200° C.–202° C. EA calculated for $C_{14}H_{17}N_3O_2$: C, 64.85; H, 6.61; N, 16.20. Found: C, 64.72; H, 6.48; N, 16.11.

Preparation 11

4-(2-Amino-5-Nitrobenzoyl)-1-Methylpiperidine

A solution of sodium metaperiodate (1.8 g, 8.5 mmol) in water (100 mL) was added dropwise to a solution of 5-nitro-3-(1-methylpiperidin-4-yl)indole (1.0 g, 3.9 mmol) and methanesulfonic acid (260 µL, 4.0 mmol) in methanol (50 mL). The solution was stirred for 2 hours at room temperature then additional sodium metaperiodate (830 mg, 3.9 mmol) was added. The resulting solution was stirred for 13 days at room temperature. The reaction mixture was poured onto 10% aqueous sodium bicarbonate solution (300 mL) and extracted with ethyl acetate. The ethyl acetate extracts were washed with 10% aqueous sodium bicarbonate solution, water, and brine, and dried over sodium sulfate. The aqueous washes were extracted with methylene chloride and dried over sodium sulfate. The dried organic extracts were filtered, combined, and concentrated in vacuo to give 900 mg of a yellow solid. Purification by flash chromatography (silica gel, methylene chloride then methylene chloride:methanol:ammonium hydroxide, 100:4:0.5) gave 685 mg (67.2%) of the title compound. mp 131° C.–132° C. EA calculated for $C_{13}H_{17}N_3O_3$: C, 59.30; H, 6.51; N, 15.96. Found: C, 59.01; H, 6.47; N, 15.79.

Preparation 12

2-Formamidyl-5-(4-Fluorobenzamidyl)benzoyl)-1-Methylpiperidine

A solution of sodium metaperiodate (2.43 g, 11.3 mmol) in water (20 ml) was added dropwise to a solution of 5-(4-fluorobenzamidyl)-3-(1-methylpiperidin-4-yl)-1H-indole hydrochloride (2.0 g, 5.2 mmol) in methanol (70 ml) and water (70 ml). Methanol (20 ml) and water (20 ml) were added to aid in stirring. The reaction mixture was stirred at room temperature for 48 hours. The precipitate was filtered and discarded. The filtrate was diluted with 10% aqueous sodium bicarbonate solution (300 ml) and extracted with ethyl acetate (3×200 ml). The organic extracts were washed with water and brine, dried over sodium sulfate, filtered and concentrated in vacuo to give 1.9 g of a dark foam. Purification by flash chromatography (silica gel, methylene chloride:methanol:ammonium hydroxide, 100:5:0.5 then 100:7.5:0.5) gave 1.0 g (50.5%) of the title compound as a white solid. MS(FD) 383 (M$^+$).

Preparation 13

2-Amino-5-(4-Fluorobenzamidyl)benzoyl)-1-Methylpiperidine

To a solution of 2-formamidyl-5-(4-fluorobenzamidyl) benzoyl)-1-methylpiperidine (500 mg, 1.3 mmol) in methanol (20 ml) was added 5N aqueous sodium hydroxide (2.6 ml, 13.0 mmol). The resulting reaction mixture was stirred at room temperature for 3 hours and 40 minutes then an additional amount of 5N aqueous sodium hydroxide (2.6 ml, 13.0 mmol) was added. The reaction mixture was stirred at room temperature for 1.5 hours, 5N aqueous sodium hydroxide (5.0 ml, 25.0 mmol) was added, and the mixture was heated at 45° C. for 1 hour. The solvent was removed under reduced pressure and the residue was dissolved in ethyl acetate. The ethyl acetate solution was washed with water and brine, dried over sodium sulfate, filtered and concentrated in vacuo to give 480 mg of a yellow oil. Purification by flash chromatography (silica gel, methylene chloride:methanol:ammonium hydroxide, 100:5:0.5) gave 460 mg (50.5%) of the title compound a yellow foam. MS(FD) 355 (M+). EA calculated for $C_{22}H_{23}ClF_2N_2$: C, 67.95; H, 6.24; N, 11.82. Found: C, 67.33; H, 6.09; N, 11.58.

EXAMPLES

Example 1

5-Nitro-3-(1-Methylpiperidin-4-yl)-1H-Indazole

To a −5° C. solution of 4-(2-amino-5-nitrobenzoyl)-1-methylpiperidine (570 mg, 2.2 mmol) in 9.6N aqueous hydrochloric acid (10 mL) was added dropwise a solution of sodium nitrite (164 mg, 2.4 mmol) in water (3 mL). This resulting diazonium salt solution was stirred 10 minutes at −5° C. then added dropwise to a −5° C. solution of stannous chloride dihydrate (1.95 g, 8.6 mmol) in 12N aqueous hydrochloric acid (6 mL). The resulting solution was stirred 2 hours at −3° C., basified with 1N aqueous sodium hydroxide (190 mL) and extracted exhaustively with ethyl acetate and methylene chloride. The combined organic extracts were dried over sodium sulfate, filtered, and concentrated in vacuo to give 420 mg of a brown residue. Purification by radial chromatography (silica gel, 2000 micron rotor, methylene chloride:methanol:ammonium hydroxide, 100:10:1) gave 177 mg (31.4%) of the title compound. The product was crystallized as the hydrochloride salt. EA calculated for $C_{13}H_{17}ClN_4O_2$: C, 52.62; H, 5.77; N, 18.88. Found: C, 52.39; H, 5.96; N, 18.77.

Example 2

5-Amino-3-(1-Methylpiperidin-4-yl)-1H-Indazole

A mixture of 5-nitro-3-(1-methylpiperidin-4-yl)-1H-indazole (287 mg, 1.1 mmol), 5N aqueous hydrochloric acid (0.5 mL), water (5 ml), and methanol (15 mL) was warmed to give a homogeneous solution. Palladium (86 mg, 5% on carbon) was added to the solution and the resulting mixture was stirred under an atmosphere of hydrogen gas for 24 hours. The palladium catalyst was filtered and the filtrate was concentrated in vacuo. The residue was slurried in methylene chloride and 5N aqueous sodium hydroxide then extracted with chloroform/isopropanol (3:1). The organic extracts were dried over sodium sulfate, filtered, and concentrated in vacuo to give 261 mg of a light brown foam. Purification by radial chromatography (silica gel, 2000 micron rotor, methylene chloride:methanol:ammonium hydroxide, 100:10:1) gave 223 mg (87.8%) of a brown oil. The product was crystallized as the dihydrochloride salt. EA calculated for $C_{13}H_{20}Cl_2N_4$: C, 51.49; H, 6.65; N, 18.48. Found: C, 51.44; H, 6.76; N, 18.47.

Example 3

5-(4-Fluorobenzamidyl)-3-(1-Methylpiperidin-4-yl)-1H-Indazole

To a 0° C. solution of 2-amino-5-(4-fluorobenzamidyl) benzoyl)-1-methylpiperidine (154 mg, 0.43 mmol) in 6N aqueous hydrochloric acid (3.2 ml) was added dropwise a solution of sodium nitrite (31 mg, 0.45 mmol) in water (1 ml). This resulting diazonium salt solution was stirred 15 minutes at 0° C. then added dropwise to a 3° C. sulfur dioxide saturated water solution. Sulfur dioxide was continually bubbled through the reaction mixture during the addition and for 20 minutes after the addition was complete. The reaction mixture was stirred at 3° C. for 1 hour then at room temperature for 20 hours. The reaction mixture was poured onto ice, basified with 5N aqueous sodium hydroxide, and extracted with methylene chloride. The organic extracts were washed with brine, dried over sodium sulfate, filtered and concentrated in vacuo to 40 mg (26.1%) of a brown foam. The title compound was crystallized as the oxalate salt. mp 151–3° C. EA calculated for $C_{22}H_{23}FN_4O_5$: C, 59.72; H, 5.24; N, 12.66. Found: C, 60.01; H, 5.30; N, 12.70.

The compounds of this invention are useful for increasing activation of the $5-HT_{1F}$ receptor. An increase in the activation of the $5-HT_{1F}$ is useful for treating a variety of disorders which have been linked to decreased neurotransmission of serotonin in mammals, e.g., migraine headaches. For further instruction on the nexus between activation of the $5-HT_{1F}$ and migraine, see the previously incorporated by reference U.S. Pat. No. 5,708,008.

To demonstrate the use of the compounds of this invention in the treatment of migraine, their ability to bind to the $5-HT_{1F}$ receptor subtype was determined. The ability of the compounds of this invention to bind to the $5-HT_{1F}$ receptor subtype was measured essentially as described in N. Adham, et al., *Proceedings of the National Academy of Sciences (USA)*, 90:408–412, 1993.

Membrane Preparation:

Membranes were prepared from transfected Ltk- cells (transfected with the human $5-HT_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford. *Anal. Biochem.*, 72:248–254, 1976.

Radioligand Binding:

[$^3$H-5-HT] binding was performed using slight modifications of the $5-HT_{1D}$ assay conditions reported by Herrick-Davis and Titeler (*J. Neurochem.*, 50:1624–1631, 1988) with the omission of masking ligands. Radioligand binding studies were achieved at 37° C. in a total volume of 250 μL of buffer (50 mM Tris, 10 mM $MgCl_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 $\mu$M 5-HT. Binding was initiated by the addition of 50 $\mu$L membrane homogenates (10–20 $\mu$g). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation. *Biochem. Pharmacol.,* 22:3099–3108, 1973. All experiments were performed in triplicate. Representative compounds of this invention were found to have affinity for the 5-HT$_{1F}$ receptor as measured by the procedure described above.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. N. Adham, et al., supra,; R. L. Weinshank, et al., *Proceedings of the National Academy of Sciences* (USA), 89:3630–3634, 1992; and the references cited therein.

Measurement of cAMP Formation:

Human 5-HT$_{1F}$ receptor transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 $\mu$M pargyline for 20 minutes at 37° C., 5% CO$_2$. Drug dose-effect curves were then conducted by adding 6 different final concentrations of drug, followed immediately by the addition of forskolin (10 $\mu$M). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 $\mu$M). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention shown to have affinity for the 5-HT$_{1F}$ receptor were tested and found to be agonists at the 5-HT$_{1F}$ receptor in the cAMP assay.

The type of formulation employed for the administration of the compounds employed in the methods of the present invention may be dictated by the particular compounds employed, the type of pharmacokinetic profile desired from the route of administration and the compound(s), and the state of the patient.

Formulations amenable to oral or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a compound of formula I.

Formulation Example 1
Hard Gelatin Capsules

| Ingredient | Quantity (mg/capsule) |
| --- | --- |
| Active ingredient | 30.0 |
| Starch | 305.0 |
| Magnesium stearate | 5.0 |

The above ingredients are mixed and filled into hard gelatin capsules in 340 mg quantities.

Formulation Example 2
Tablet

| Ingredient | Quantity (mg/tablet) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3
Dry Powder Inhaler

| Ingredient | Weight % |
| --- | --- |
| Active ingredient | 5 |
| Lactose | 95 |

The active ingredient is mixed with the lactose and the mixture is added to a dry powder inhaling appliance.

Formulation Example 4
Tablet

| Ingredient | Quantity (mg/tablet) |
| --- | --- |
| Active ingredient | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5
Capsules

| Ingredient | Quantity (mg/capsule) |
| --- | --- |
| Active ingredient | 40.0 |
| Starch | 109.0 |
| Magnesium Stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6
Suppositories

| Ingredient | Amount |
| --- | --- |
| Active ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7
Suspensions

| Ingredient | Amount |
| --- | --- |
| Active ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Formulation Example 8 Capsules | |
| --- | --- |
| Ingredient | Quantity (mg/capsule) |
| Active ingredient | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

| Formulation Example 9 Intravenous Formulation | |
| --- | --- |
| Ingredient | Quantity |
| Active ingredient | 250.0 mg |
| Isotonic saline | 1000 ml |

| Formulation Example 10 Topical Formulation | |
| --- | --- |
| Ingredient | Quantity |
| Active ingredient | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

| Formulation Example 11 Sublingual or Buccal Tablets | |
| --- | --- |
| Ingredient | Quantity (mg/tablet) |
| Active ingredient | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of formula I:

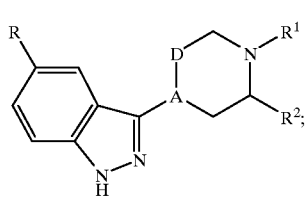

or a pharmaceutical acid addition salt thereof; where:

A—D is CH—$CH_2$ or C=CH;

R is $NR^3C(O)R^4$, $NR^3SO_2R^5$, $NHC(O)NR^6R^7$, $NHC(S)NR^6R^7$, or $NHCO_2R^8$;

$R^1$ is hydrogen or $C_1$–$C_6$ alkyl;

$R^2$ is hydrogen or $R^1$ and $R^2$ combine, together with the 6 membered ring to which they are attached, to form a 6:5, 6:6, or 6:7 fused bicyclic ring;

$R^3$ is hydrogen or $C_1$–$C_6$ alkyl;

$R^4$ is $C_1$–$C_6$ alkyl, $C_3$–$C_6$ alkenyl; $C_3$–$C_6$ cycloalkyl; phenyl($C_1$–$C_4$ alkylene); $C_1$–$C_4$ alkyl ω-substituted with phenoxy; $C_1$–$C_4$ alkyl ω-substituted with $C_1$–$C_4$ alkoxy; phenyl monosubstituted with halo; phenyl monosubstituted with $C_1$–$C_4$ alkoxy; phenyl monosubstituted with $C_1$–$C_4$ alkyl, $C_1$–$C_4$ alkylthio, or $C_1$–$C_4$ acyl; phenyl disubstituted with substitutents selected from halo, $C_1$–$C_4$ alkyl, $C_1$–$C_4$ alkoxy and nitro; heterocycle; furyl optionally substituted with $C_1$–$C_4$ alkyl, $C_1$–$C_4$ alkoxy, or halo; thienyl optionally substituted with halo, $C_1$–$C_4$ alkyl or $C_1$–$C_4$ alkoxy; or pyridinyl optionally substituted with halo, $C_1$–$C_4$ alkyl or $C_1$–$C_4$ alkoxy;

$R^5$ is $C_1$–$C_6$ alkyl, phenyl, substituted phenyl, or ($C_1$–$C_6$ alkyl)$_2$amino;

$R^6$ and $R^7$ are independently $C_1$–$C_6$ alkyl, $C_3$–$C_6$ alkenyl, $C_3$–$C_8$ cycloalkyl, phenyl, substituted phenyl, phenyl ($C_1$–$C_4$ alkyl), or substituted phenyl($C_1$–$C_4$ alkyl), or $R^6$ and $R^7$ combine, together with the nitrogen atom to which they are attached, to form a pyrrolidine, piperidine, piperazine, 4-substituted piperazine, morpholine or thiomorpholine ring;

$R^8$ is $C_1$–$C_6$ alkyl, $C_3$–$C_6$ alkenyl, phenyl, substituted phenyl, or $C_3$–$C_8$ cycloalkyl.

2. The compound of claim 1 where A—D is CH—$CH_2$, $R^1$ is $C_1$–$C_4$ alkyl, and $R^2$ is hydrogen; or a pharmaceutical acid addition salt thereof.

3. The compound of claim 2 where R is $NR^3C(O)R^4$ and $R^1$ is methyl; or a pharmaceutical acid addition salt thereof.

4. The compound of claim 3 where $R^3$ is hydrogen and $R^4$ is $C_1$–$C_4$ alkyl, $C_3$–$C_6$ alkenyl, $C_3$–$C_8$ cycloalkyl, or phenyl monosubstituted with $C_1$–$C_4$ alkoxy or halo; or a pharmaceutical acid addition salt thereof.

5. The compound of claim 4 where $R^4$ is selected from: methyl, ethyl, propyl, allyl, cyclopentyl, 4-methoxyphenyl, and 4-fluorophenyl; or a pharmaceutical acid addition salt thereof.

6. The compound of claim 1 where A—D is CH—$CH_2$ and $R^1$ and $R^2$ combine, together with the 6 membered ring to which they are attached, to form a 6:5 or 6:6 fused bicyclic ring; or a pharmaceutical acid addition salt thereof.

7. A pharmaceutical formulation comprising a compound of formula I

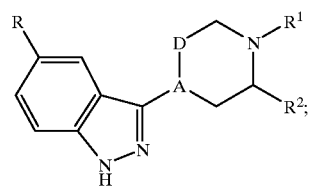

or a pharmaceutical acid addition salt thereof; where:

A—D is CH—$CH_2$ or C=CH;

R is $NR^3C(O)R^4$, $NR^3SO_2R^5$, $NHC(O)NR^6R^7$, $NHC(S)NR^6R^7$, or $NHCO_2R^8$;

$R^1$ is hydrogen or $C_1$–$C_6$ alkyl;

$R^2$ is hydrogen or $R^1$ and $R^2$ combine, together with the 6 membered ring to which they are attached, to form a 6:5, 6:6, or 6:7 fused bicyclic ring;

$R^3$ is hydrogen or $C_1$–$C_6$ alkyl;

$R^4$ is $C_1$–$C_6$ alkyl, $C_3$–$C_6$ alkenyl; $C_3$–$C_6$ cycloalkyl; phenyl($C_1$–$C_4$ alkylene); $C_1$–$C_4$ alkyl (ω-substituted with phenoxy; $C_1$–$C_4$ alkyl ω-substituted with $C_1$–$C_4$ alkoxy; phenyl monosubstituted with halo; phenyl monosubstituted with $C_1$–$C_4$ alkoxy; phenyl monosubstituted with $C_1$–$C_4$ alkyl, $C_1$–$C_4$ alkylthio, or $C_1$–$C_4$ acyl; phenyl disubstituted with substitutents selected from halo, $C_1$–$C_4$ alkyl, $C_1$–$C_4$ alkoxy and nitro; heterocycle; furyl optionally substituted with $C_1$–$C_4$ alkyl, $C_1$–$C_4$ alkoxy, or halo; thienyl optionally substituted with halo, $C_1$–$C_4$ alkyl or $C_1$–$C_4$ alkoxy; or pyridinyl optionally substituted with halo, $C_1$–$C_4$ alkyl or $C_1$–$C_4$ alkoxy;

$R^5$ is $C_1$–$C_6$ alkyl, phenyl, substituted phenyl, or ($C_1$–$C_6$ alkyl)$_2$amino;

$R^6$ and $R^7$ are independently $C_1$–$C_6$ alkyl, $C_3$–$C_6$ alkenyl, $C_3$–$C_8$ cycloalkyl, phenyl, substituted phenyl, phenyl ($C_1$–$C_4$ alkyl), or substituted phenyl ($C_1$–$C_4$ alkyl), or $R^6$ and $R^7$ combine, together with the nitrogen atom to which they are attached, to form a pyrrolidine, piperidine, piperazine, 4-substituted piperazine, morpholine or thiomorpholine ring;

$R^8$ is $C_1$–$C_6$ alkyl, $C_3$–$C_6$ alkenyl, phenyl, substituted phenyl, or $C_3$–$C_8$ cycloalkyl; and a pharmaceutical carrier, diluent, or excipient.

8. A method for activating 5-$HT_{1F}$ receptors in a mammal comprising administering to a mammal in need of such activation an effective amount of a compound of a compound of formula I

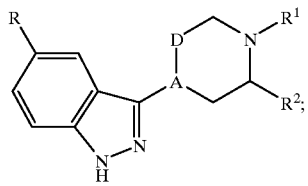

or a pharmaceutical acid addition salt thereof; where:
A—D is CH—CH$_2$ or C=CH;
R is NR$^3$C(O)R$^4$, NR$^3$SO$_2$R$^5$, NHC(O)NR$^6$R$^7$, NHC(S)NR$^6$R$^7$, or NHCO$_2$R$^8$;
R$^1$ is hydrogen or C$_1$–C$_6$ alkyl;
R$^2$ is hydrogen or R$^1$ and R$^2$ combine, together with the 6 membered ring to which they are attached, to form a 6:5, 6:6, or 6:7 fused bicyclic ring;
R$^3$ is hydrogen or C$_1$–C$_6$ alkyl;
R$^4$ is alkyl, C$_3$–C$_6$ alkenyl; C$_3$–C$_6$ cycloalkyl; phenyl (C$_1$–C$_4$ alkylene); C$_1$–C$_4$ alkyl ω-substituted with phenoxy; C$_1$–C$_4$ alkyl ω-substituted with C$_1$–C$_4$ alkoxy; phenyl monosubstituted with halo; phenyl monosubstituted with C$_1$–C$_4$ alkoxy; phenyl monosubstituted with C$_1$–C$_4$ alkyl, C$_1$–C$_4$ alkylthio, or C$_1$–C$_4$ acyl; phenyl disubstituted with substitutents selected from halo, C$_1$–C$_4$ alkyl, C$_1$–C$_4$ alkoxy and nitro; heterocycle; furyl optionally substituted with C$_1$–C$_4$ alkyl, C$_1$–C$_4$ alkoxy, or halo; thienyl optionally substituted with halo, C$_1$–C$_4$ alkyl or C$_1$–C$_4$ alkoxy; or pyridinyl optionally substituted with halo, C$_1$–C$_4$ alkyl or C$_1$–C$_4$ alkoxy;
R$^5$ is C$_1$–C$_6$ alkyl, phenyl, substituted phenyl, or (C$_1$–C$_6$ alkyl)$_2$amino;
R$^6$ and R$^7$ are independently C$_1$–C$_6$ alkyl, C$_3$–C$_6$ alkenyl, C$_3$–C$_8$ cycloalkyl, phenyl, substituted phenyl, phenyl (C$_1$–C$_4$ alkyl), or substituted phenyl (C$_1$–C$_4$ alkyl), or R$^6$ and R$^7$ combine, together with the nitrogen atom to which they are attached, to form a pyrrolidine, piperidine, piperazine, 4-substituted piperazine, morpholine or thiomorpholine ring;
R$^8$ is C$_1$–C$_6$ alkyl, C$_3$–C$_6$ alkenyl, phenyl, substituted phenyl, or C$_3$–C$_8$ cycloalkyl.

9. The method according to claim 8 where the mammal is a human.

10. A method for inhibiting neuronal protein extravasation in a mammal comprising administering to a mammal in need of such inhibition an effective amount of a compound of formula I:

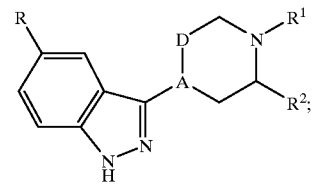

or a pharmaceutical acid addition salt thereof; where:
A—D is CH—CH$_2$ or C=CH;
R is NR$^3$C(O)R$^4$, NR$^3$SO$_2$R$^5$, NHC(O)NR$^6$R$^7$, NHC(S)NR$^6$R$^7$, or NHCO$_2$R$^8$;
R$^1$ is hydrogen or C$_1$–C$_6$ alkyl;
R$^2$ is hydrogen or R$^1$ and R$^2$ combine, together with the 6 membered ring to which they are attached, to form a 6:5, 6:6, or 6:7 fused bicyclic ring;
R$^3$ is hydrogen or C$_1$–C$_6$ alkyl;
R$^4$ is C$_1$–C$_6$ alkyl, C$_3$–C$_6$ alkenyl; C$_3$–C$_6$ cycloalkyl; phenyl(C$_1$–C$_4$ alkylene); C$_1$–C$_4$ alkyl ω-substituted with phenoxy; C$_1$–C$_4$ alkyl ω-substituted with C$_1$–C$_4$ alkoxy; phenyl monosubstituted with halo; phenyl monosubstituted with C$_1$–C$_4$ alkoxy; phenyl monosubstituted with C$_1$–C$_4$ alkyl, C$_1$–C$_4$ alkylthio, or C$_1$–C$_4$ acyl; phenyl disubstituted with substitutents selected from halo, C$_1$–C$_4$ alkyl, C$_1$–C$_4$ alkoxy and nitro; heterocycle; furyl optionally substituted with C$_1$–C$_4$ alkyl, C$_1$–C$_4$ alkoxy, or halo; thienyl optionally substituted with halo, C$_1$–C$_4$ alkyl or C$_1$–C$_4$ alkoxy; or pyridinyl optionally substituted with halo, C$_1$–C$_4$ alkyl or C$_1$–C$_4$ alkoxy;
R$^5$ is C$_1$–C$_6$ alkyl, phenyl, substituted phenyl, or (C$_1$–C$_6$ alkyl)$_2$amino;
R$^6$ and R$^7$ are independently C$_1$–C$_6$ alkyl, C$_3$–C$_6$ alkenyl, C$_3$–C$_8$ cycloalkyl, phenyl, substituted phenyl, phenyl (C$_1$–C$_4$ alkyl), or substituted phenyl(C$_1$–C$_4$ alkyl), or R$^6$ and R$^7$ combine, together with the nitrogen atom to which they are attached, to form a pyrrolidine, piperidine, piperazine, 4-substituted piperazine, morpholine or thiomorpholine ring;
R$^8$ is C$_1$–C$_6$ alkyl, C$_3$–C$_6$ alkenyl, phenyl, substituted phenyl, or C$_3$–C$_8$ cycloalkyl.

11. The method according to claim 10 where the mammal is a human.

* * * * *

UNITED STATES PATENT AND TRADEMARK OFFICE
CERTIFICATE OF CORRECTION

PATENT NO.     : 6,133,290
DATED          : October 17, 2000
INVENTOR(S)    : Krushinski, Jr. et al.

Page 1 of 1

It is certified that error appears in the above-identified patent and that said Letters Patent is hereby corrected as shown below:

<u>Column 29,</u>
Line 21, "$R^4$ is alkyl…" should read -- $R^4$ is $C_1$-$C_6$ alkyl… --

Signed and Sealed this

Second Day of September, 2003

JAMES E. ROGAN
*Director of the United States Patent and Trademark Office*